US012796956B2

(12) United States Patent
Sabczynski et al.

(10) Patent No.: US 12,796,956 B2
(45) Date of Patent: Nov. 17, 2026

(54) ENDOBRONCHIAL FLOW MEAUREMENT AND FLOW CONTROL FOR REGIONAL VENTILATION

(71) Applicant: KONINKLIJKE PHILIPS N.V., Eindhoven (NL)

(72) Inventors: Joerg Sabczynski, Hamburg (DE); Bernhard Gleich, Hamburg (DE); Juergen Erwin Rahmer, Hamburg (DE); Thomas Koehler, Hamburg (DE); Rafael Wiemker, Hamburg (DE); Roberto Buizza, Eindhoven (NL); Cornelis Petrus Hendriks, Eindhoven (NL); Jaap Roger Haartsen, Eindhoven (NL); Nataly Wieberneit, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 572 days.

(21) Appl. No.: 18/112,164

(22) Filed: Feb. 21, 2023

(65) Prior Publication Data

US 2023/0404432 A1 Dec. 21, 2023

Related U.S. Application Data

(60) Provisional application No. 63/346,341, filed on May 27, 2022.

(51) Int. Cl.
*A61B 5/087* (2006.01)
*A61B 5/00* (2006.01)

(52) U.S. Cl.
CPC .......... *A61B 5/0876* (2013.01); *A61B 5/6862* (2013.01); *A61B 5/7278* (2013.01);
(Continued)

(58) Field of Classification Search
CPC ... A61B 5/0876; A61B 5/6862; A61B 5/7278; A61B 2562/0223; A61B 2562/0247
(Continued)

(56) References Cited

U.S. PATENT DOCUMENTS 9,339,618 B2 5/2016 Deem
10,799,092 B2 10/2020 Krimsky
(Continued)

FOREIGN PATENT DOCUMENTS

CN 113941063 A1 1/2022
WO 2010017685 A1 2/2010
(Continued)

OTHER PUBLICATIONS

International Search Report for PCT/EP2023/063788 filed May 23, 2023.

(Continued)

*Primary Examiner* — Chanel J Yoon
(74) *Attorney, Agent, or Firm* — Daniel H. Brean

(57) ABSTRACT

A medical device for treating an associated patient includes a bronchial sensor device configured to measure fluid pressure in a bronchus of the associated patient; and an electronic controller configured to: receive the fluid pressure data from the bronchial sensor device; and calculate a fluid flow measurement through the bronchus based on the measured fluid pressure.

8 Claims, 7 Drawing Sheets

(52) U.S. Cl.
CPC ................ *A61B 2562/0223* (2013.01); *A61B 2562/0247* (2013.01)

(58) Field of Classification Search
USPC ........................................................ 600/538
See application file for complete search history.

(56) References Cited

U.S. PATENT DOCUMENTS

| | | | | |
|---|---|---|---|---|
| 2003/0127090 | A1 | 7/2003 | Gifford | |
| 2011/0270116 | A1* | 11/2011 | Freitag | A61B 5/6852 600/538 |
| 2016/0263391 | A1 | 9/2016 | Tasci | |
| 2019/0365325 | A1 | 12/2019 | Reiner | |
| 2021/0244305 | A1 | 8/2021 | Gleich | |
| 2022/0039752 | A1 | 2/2022 | Hunter | |
| 2023/0201502 | A1 | 6/2023 | Enk | |

FOREIGN PATENT DOCUMENTS

| | | | | |
|---|---|---|---|---|
| WO | 2017075009 | A1 | 5/2017 | |
| WO | WO-2020253977 | A1 * | 12/2020 | G01L 19/14 |

OTHER PUBLICATIONS

Noma, H. et al., "Development of Stent Flow Sensor Device Evaluating Breathing Property at Airway in Experimental Animal Under Free Move Condition." IEEE MEMS 2020, Jan. 18-22, 2020, Vancouver, Canada.

Greenblatt, E.E. et al., "Pendelluft in the Bronchial Tree," Journal of Applied Physiology: Respiratory, Environment and Exercise Physiology, 117.9 (Aug. 2014), 979-88.

Rahmer, J. et al., "Spatially Selective Remote Magnetic Actuation of Identical Helical Micromachines.," Science Robotics, 2.3 (2017). Abstract.

Rahmer, J. et al., "Remote Magnetic Actuation Using a Clinical Scale System" PLOS One, 13.3 (2018).

'Olympus_Spiration-Valve-System-FDA-Approved.Jpg (JPEG Image, 350 × 306 Pixels)' <https://medical.olympusamerica.com/sites/default/files/us/files/pictures/Olympus_Spiration-Valve-System-FDA-approved.jpg> [accessed Aug. 17, 2021].

Koster, T.D. et al., 'The Fissure: Interlobar Collateral Ventilation and Implications for Endoscopic Therapy in Emphysema', International Journal of Chronic Obstructive Pulmonary Disease, 11 (2016), 765 <https://doi.org/10.2147/COPD.S103807>.

* cited by examiner

ENDOBRONCHIAL FLOW MEAUREMENT AND FLOW CONTROL FOR REGIONAL VENTILATION

CROSS-REFERENCE TO RELATED APPLICATIONS

This patent application claims the priority benefit under 35 U.S.C. § 119(e) of U.S. Provisional Application No. 63/346,341, filed on May 27, 2022, the contents of which are herein incorporated by reference.

The following relates generally to the respiratory therapy arts, mechanical ventilation arts, mechanical ventilation control arts, endobronchial valve arts, and related arts.

BACKGROUND

Invasive mechanical ventilation is a key component of intensive care. Several different methods of ventilation exist, which differ in several variables: Ventilation can be distinguished by the way how a breath is triggered (pressure, volume, flow), by the limits (on volume, pressure, or flow) that should not be exceeded, and the cycle factors terminating an inspiration (again pressure, volume, flow, time). There exist volume-targeted ventilator modes, pressure targeted modes, as well as combined modes. An amount of Positive End-Expiratory Pressure (PEEP) is an important factor as well. The intensivist has thus many ventilation parameters at hand to optimally care for the individual patient.

However, all of these different ventilation modes and parameters provide air, pressure, volume, and flow via a single interface to the patient body: the trachea and therein an endotracheal tube (ETT) for invasive ventilation. The distribution of the insufflated air volume within the lung depends on the local airway resistance and the regional compliance of the respiratory system. In some diseases, one or both of the local airway resistance and the regional compliance are heterogenous, thus leading to heterogeneous distribution of the insufflated volume. This can lead to the situation that in some regions the PEEP value is too low for lung recruitment, while in other regions the pressure is too high and leads to lung overdistention or to cardiac complications. Examples are patients having lobar pneumonia, lobar atelectasis, or other asymmetrical pulmonary problems. Patients with e.g. ARDS (Acute Respiratory Distress Syndrome) often develop an edema, which due to gravity-induced pressure can lead to poorly inflated or collapsed pulmonary units of the dependent lung regions.

Inhomogeneous inflation or deflation of the lungs can also cause dynamic pressure differences between regions and lead to interregional airflows known as pendelluft (see, e.g., Elliot E. Greenblatt et al., 'Pendelluft in the Bronchial Tree,' Journal of Applied Physiology, 117.9 (2014), 979-88 https://doi.org/10.1152/japplphysiol.00466.2014). This may be an important phenomenon contributing to regional gas exchange, irreversible mixing, and aerosol deposition patterns inside poorly ventilated regions of the lung. It is more prominent in diseases with a significant heterogeneity in both resistance and compliance.

In addition, COPD (Chronic Obstructive Pulmonary Disease) is a progressive lung disease associated with emphysema. Emphysema is characterized by air-filled spaces in the lung and permanent damage to the lung tissue. Emphysematous parts of the lung can hyperinflate. In consequence, other healthier parts of the lung have less space in the thorax and can thus not participate adequately in gas exchange leading to shortness of breath. Therefore, the surgical removal of the lobe most affected by emphysema (lung volume reduction surgery) can be an effective treatment for severe COPD.

The implantation of endobronchial valves is a minimally-invasive alternative to lung volume reduction surgery and is also called Bronchoscopic Lung Volume Reduction (BLVR). One or more endobronchial valves are placed bronchoscopically (i.e. under visual control) in one or more bronchi. These valves are simple one-way valves, which allow the air to be breathed out, but not breathed in. After implantation, the target lobe rapidly collapses (if there is no pulmonary shunt) and gives space to more healthy lobes. Several valve systems are on the market (e.g., from Olympia Spiration, Pulmonx, and so forth). Endobronchial valves can easily be placed and removed again with a dedicated catheter through the working channel of the bronchoscope.

As such, there are many situations in intensive care, in which it would be favorable that a ventilated patient could get regionally targeted ventilation volume. However, it is not possible with current ventilation systems to locally measure the pressure, flow, or volume reaching a subunit of the lung (e.g. a lobe or a segment). It is also not possible to target parts of the lung with a dedicated parameter setting (e.g. pressure, volume, or flow) or with a dedicated pressure, flow, or volume curve.

The following discloses certain improvements to overcome these problems and others.

SUMMARY

In one aspect, a medical device for treating an associated patient includes a bronchial sensor device configured to measure fluid pressure in a bronchus of the associated patient; and an electronic controller configured to: receive the fluid pressure data from the bronchial sensor device; and calculate a fluid flow measurement through the bronchus based on the measured fluid pressure.

In another aspect, a medical device for treating an associated patient includes a bronchial sensor device for placement in a bronchus of the associated patient and configured to measure fluid pressure in the bronchus. The bronchial sensor device includes a base; a membrane connected to the base; and a micro-bot actuator connected to the membrane. An electronic controller is configured to receive the fluid pressure data from the bronchial sensor device; and calculate a fluid flow measurement through the bronchus based on a distance between the membrane and the base measured by the micro-bot actuator.

One advantage resides in providing patients undergoing mechanical ventilation therapy with a regionally targeted ventilation volume.

Another advantage resides in providing a mechanical ventilation system that can locally measure pressure, flow, or volume reaching a subunit of the lung.

Another advantage resides in targeting parts of a lung with a dedicated parameter setting (e.g. pressure, volume, or flow) or with a dedicated pressure, flow, or volume curve for a patient undergoing mechanical ventilation therapy.

Another advantage resides in automatically adjusting settings of a mechanical ventilator to help wean patients off mechanical ventilation therapy.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

Figure 1:
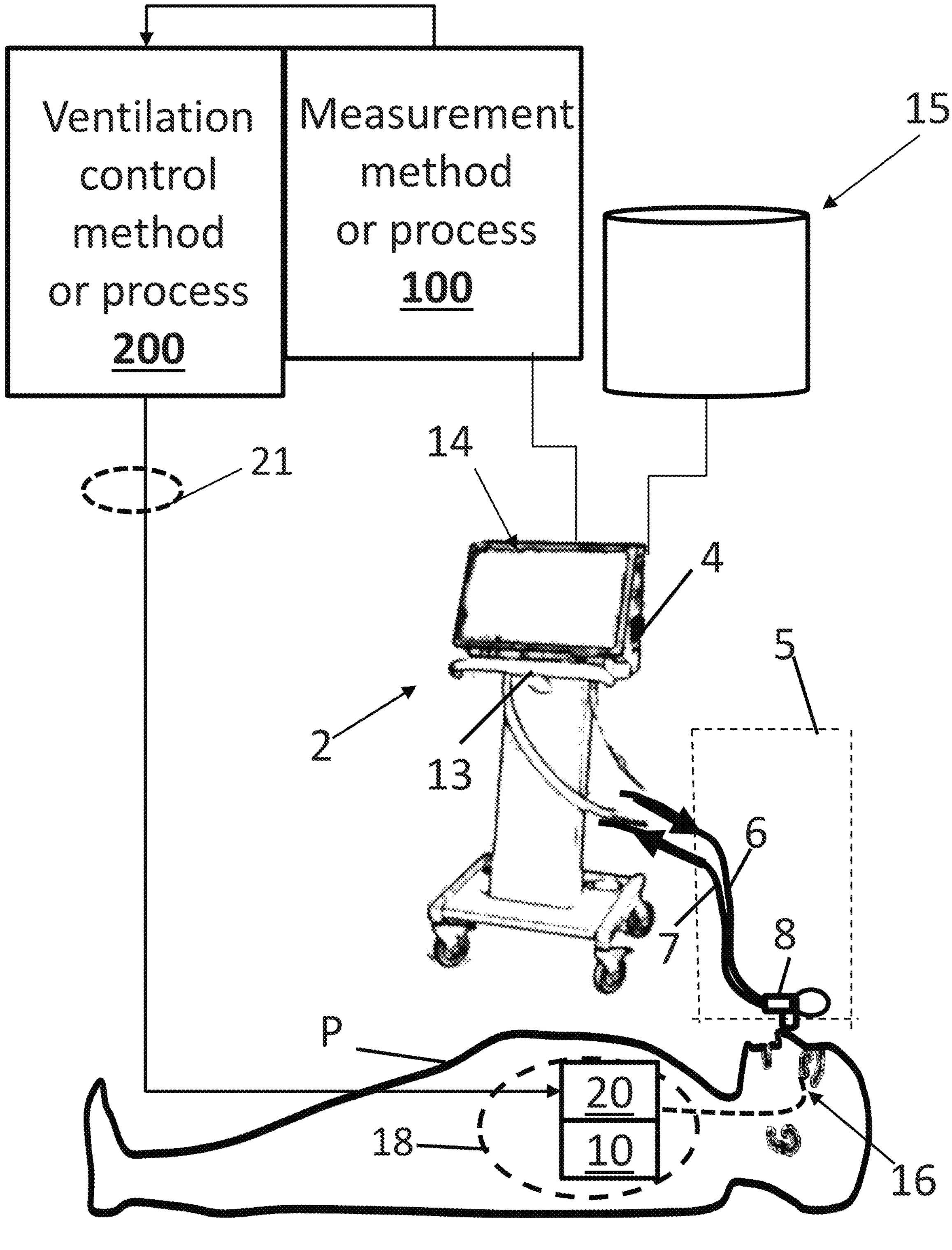
FIG. 1 diagrammatically shows an illustrative mechanical ventilation system in accordance with the present disclosure.

As used herein, the singular form of "a," "an," and "the" include plural references unless the context clearly dictates otherwise. As used herein, statements that two or more parts or components are "coupled," "connected," or "engaged" shall mean that the parts are joined, operate, or co-act together either directly or indirectly, i.e., through one or more intermediate parts or components, so long as a link occurs. Directional phrases used herein, such as, for example and without limitation, top, bottom, left, right, upper, lower, front, back, and derivatives thereof, relate to the orientation of the elements shown in the drawings and are not limiting upon the scope of the claimed invention unless expressly recited therein. The word "comprising" or "including" does not exclude the presence of elements or steps other than those described herein and/or listed in a claim. In a device comprised of several means, several of these means may be embodied by one item of hardware.

In order to provide a regional measurement of ventilation parameters for a patient undergoing mechanical ventilation therapy, one or more measurement devices are placed endobronchially (i.e. with the help of a bronchoscope) in one or more of the lobar bronchi or segmental bronchi or even smaller bronchi. The measurement device is placed and fixed endobronchially. It contains one or more pressure sensors, preferably based on Micro-Bot technology (see, e.g., J Rahmer, C Stehning, and B Gleich, 'Spatially Selective Remote Magnetic Actuation of Identical Helical Micromachines,' Science Robotics, 2.3 (2017)), which can be read out wirelessly and do not need a built-in power supply (see, e.g., US 2021/0244305, which is incorporated herein in its entirety by reference). The measurement device is based on Bernoulli's principle and the configuration of the pressure sensors in the measurement device depends on the physical quantity to be measured, e.g. pressure and flow. Typically, the measurement device has some sort of known constriction, which adds a defined resistor to the airflow. The pressure signal from the pressure sensors is read out and transmitted to a computer, which calculates regional e.g. time-pressure, time-flow, and time-volume curves. Alternatively, regional ventilation parameters can be assessed with the help of imaging devices.

In addition, ventilators can provide ventilation only via the trachea to the lungs in total. Thus, they can ventilate only with a single time-pressure or time-volume curve. To provide individual pressure, volume, or flow to different lung regions (lobes, segments, or even subsegmental regions), one or more control devices are placed endobronchially. These control devices can shape ventilation parameters like pressure, volume, or flow by adapting (typically increasing) the resistance of the airway or acting as a valve and fully closing the airway.

The control device contains one or more actuators, preferably based on Micro-Bot technology, which can be switched wirelessly without built-in power supply (see, e.g., Jurgen Rahmer, Christian Stehning, and Bernhard Gleich, 'Remote Magnetic Actuation Using a Clinical Scale System,' PLOS ONE, 13.3 (2018)). The switching or resistance change is controlled by a computer. This controller may work independently (sensing the ventilator actions), or may be digitally connected to the mechanical ventilator such that the timing and strength of valve actions are in synchrony with the ventilation.

As disclosed herein, in a preferred embodiment, a measurement device and a control device are combined in one device allowing to measure and shape regional ventilation parameters in real-time. The system can work in an open and a closed loop manner and can work continuously or intermittently. Both, measurement and control devices can be built based on Micro-Bot technology comprising magneto-mechanical oscillators, which enable building tiny (1-2 mm in length) wireless markers and sensors that can be interrogated remotely using magnetic fields. Micro-bots can be built such that physical quantities like pressure are influencing their oscillation frequency, which can be detected from the outside. They do not require a power supply and are thus ideal for the application of providing regional ventilation.

With reference to FIG. 1, a mechanical ventilator 2 for providing ventilation therapy to an associated patient P is shown. As shown in FIG. 1, the mechanical ventilator 2 includes an outlet 4 connectable with a patient breathing circuit 5 to delivery mechanical ventilation to the patient P. The patient breathing circuit 5 includes typical components for a mechanical ventilator, such as an inlet line 6, an optional outlet line 7 (this may be omitted if the ventilator employs a single-limb patient circuit), a connector or port 8 for connecting with an endotracheal tube (ETT) 16 inserted into the trachea of the patient P (or, alternatively, connecting to a tracheostomy tube, not shown), and one or more breathing sensors (not shown), such as a gas flow meter, a pressure sensor, end-tidal carbon dioxide ($etCO_2$) sensor, and/or so forth. The mechanical ventilator 2 is designed to deliver air, an air-oxygen mixture, or other breathable gas (supply not shown) to the outlet 4 at a programmed pressure and/or flow rate to ventilate the patient via an ETT. The mechanical ventilator 2 also includes an electronic controller 13 (e.g., an electronic processor or a microprocessor), a display device 14, and a non-transitory computer readable medium 15 storing instructions executable by the electronic controller 13. The instructions can include fluid (e.g., liquid or gas) flow measurement method or process 100.

FIG. 1 diagrammatically illustrates the patient P intubated with an ETT 16 (the lower portion of which is inside the patient P and hence is shown in phantom). The connector or port 8 connects with the ETT 16 to operatively connect the mechanical ventilator 2 to deliver breathable air to the patient P via the ETT 16. The mechanical ventilation provided by the mechanical ventilator 2 via the ETT 16 may be therapeutic for a wide range of conditions, such as various types of pulmonary conditions like emphysema or pneumonia, viral or bacterial infections impacting respiration such as a COVID-19 infection or severe influenza, cardiovascular conditions in which the patient P receives breathable gas enriched with oxygen, or so forth.

FIG. 1 also shows an endobronchial sensor 10 (diagrammatically shown in FIG. 1 as a rectangle) disposed in a bronchus (not shown) of diagrammatically indicated lungs 18 of the patient P. The sensor 10 comprises a bronchial sensor device 10 configured to measure fluid pressure in the bronchus of the patient P. Embodiments of the bronchial sensor device 10 are described herein. FIG. 1 also shows a magneto-mechanical endobronchial valve 20 (also diagrammatically shown in FIG. 1 as a rectangle) disposed in the same or a different bronchus of the lungs 18 of the patient P. Embodiments of the endobronchial valve 20 are also described herein.

The non-transitory computer readable medium 15 of the mechanical ventilator 2 stores instructions executable by the electronic controller 13 of the mechanical ventilator 2 perform a measurement method or process 100. To do so, the measurement method 100 performed by the electronic controller 13 includes receiving the fluid pressure data from the bronchial sensor device 10, and calculating a fluid flow measurement through the bronchus based on the measured fluid pressure. In one embodiment, an indication of the fluid flow measurement can be displayed on the display device 14 of the mechanical ventilator 2. In another embodiment, the fluid flow measurement can be input to the electronic controller 13 to control operation of the mechanical ventilator in delivery mechanical ventilation therapy to the patient P. For example, if the fluid flow measurement underruns a predetermined fluid flow threshold, the mechanical ventilator 2 can be controlled to provide additional air to the patient P. whereas if the fluid flow measurement is equal to or exceeds the predetermined fluid flow threshold, the mechanical ventilator 2 can be controlled to provide a lower quantity of air to the patient P.

The non-transitory computer readable medium 15 of the mechanical ventilator 2 optionally further stores instructions executable by the electronic controller 13 of the mechanical ventilator 2 perform a ventilation control method or process 100. To do so, the control method 200 performed by the electronic controller 13 includes the receiving of the fluid flow measurement calculated by the measurement process 100 and, based on that measurement along with other information such as settings of the mechanical ventilator 2, global ventilation flow measurements acquired by gas flow, pressure, et$CO_2$, or other sensors of the ventilator 2 generates a control signal 21 for controlling the mechanical ventilation of the patient. In one example, at least one setting of the mechanical ventilator 2 is controlled based on the fluid flow measurement through the bronchus acquired by the method 100. For example, if the fluid flow measurement indicates that a portion of the lungs 18 may be receiving too much gas flow then the settings of the ventilator 2 may be adjusted to reduce the gas flow measured by the method 100 until it reaches a target level. In another example, if the gas flow measured by the method 100 is too high then the endobronchial valve 20 (which in this example may be in the same bronchus as the sensor 10) may be actuated to close (completely or partially, depending on the valve type), thereby reducing or eliminating the gas flow through that bronchus. In other examples, at least one setting of the mechanical ventilator 2 can be controlled based on one or more of the measured fluid pressure in the bronchus, the calculated fluid flow measurement through the bronchus, a determined volume of fluid in the bronchus, and other measured or derived parameters.

With reference successively to FIGS. 2-5, some nonlimiting illustrative embodiments of the sensor 10 are described.

Figure 2:
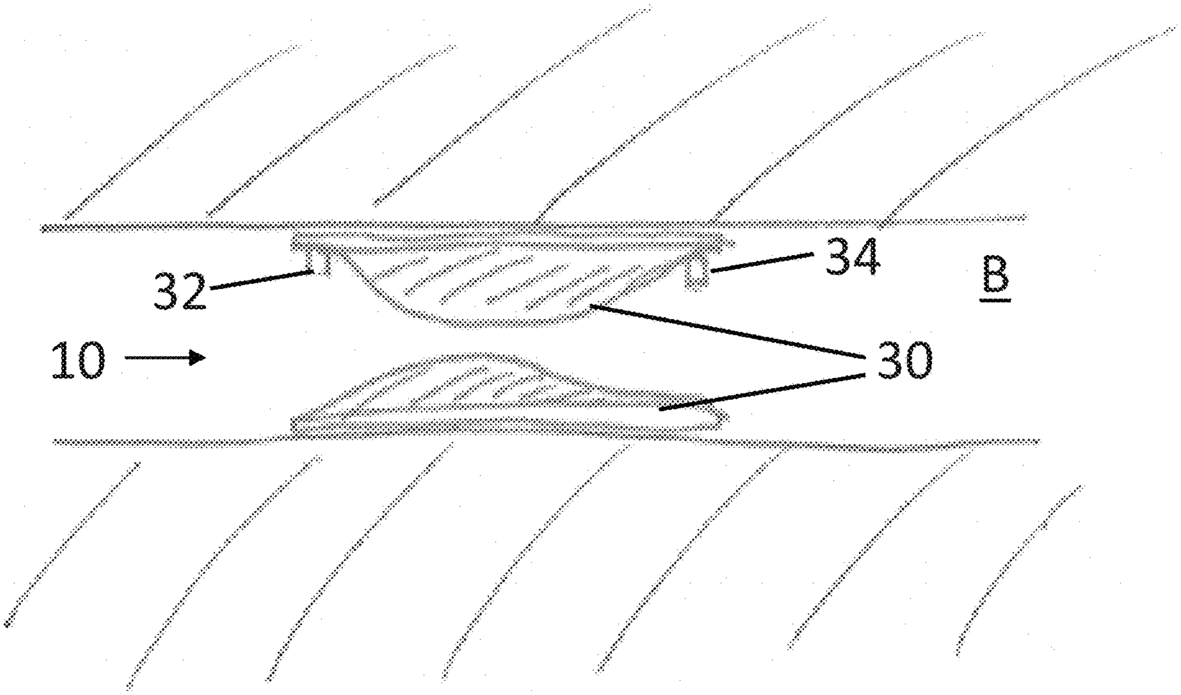
FIGS. 2-5 show example sensor devices used in the system of FIG. 1.

FIG. 2 shows one example of the bronchial sensor device 10. As shown in FIG. 2, the bronchial sensor device 10 is disposed in the bronchus B of the patient P. In one example, the bronchial sensor device 10 includes a stent 30 having a diameter smaller than a diameter of the bronchus B. A pressure sensor 32, 34 is disposed proximate to each end of the stent 30. Each pressure sensor 32, 34 comprises a magneto-mechanical oscillator device (i.e., a Micro-Bot). The electronic controller 13 is configured to calculate the fluid flow measurement based on a diameter of the stent 30 and pressure data measured by each pressure sensor 32, 34. The stent 30 acts a constriction of the airway in the bronchus B. According to Bernoulli's law, flow can be calculated from the measured pressure difference over a known resistance, in this case the stent 30 with the known diameter. In another example, the stent 30 has a diameter slightly larger than the diameter of the bronchus B such that the stent 30 dilates the bronchus B upon insertion therein.

Figure 3:
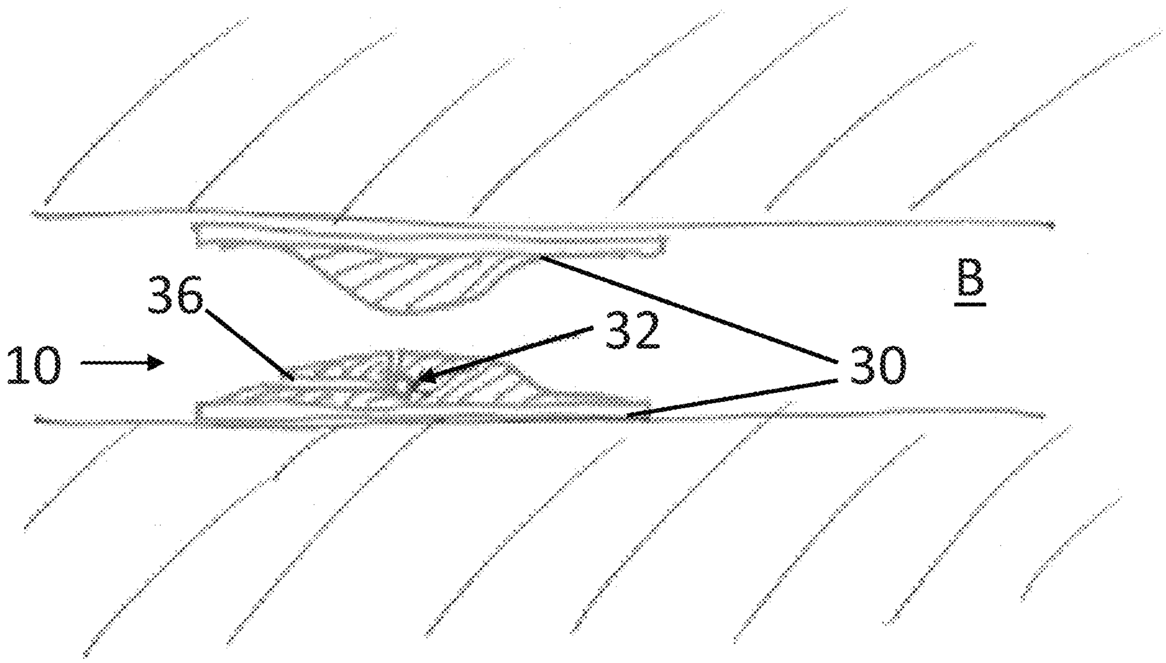

FIG. 3 shows another example of the bronchial sensor device 10. As shown in FIG. 3, the bronchial sensor device 10 is disposed in the bronchus B of the patient P. The bronchial sensor device 10 includes a tube 36 extending from an end of the stent 30 to a constriction (for air flow) in the stent 30. A single magneto-mechanical oscillator device 32 is shown (although two or more could be included) and is configured to measure a pressure difference between ends of the constriction in the stent 30. If the magneto-mechanical oscillator device 32 is placed in the tube 36 from one un-constricted end of the stent 30 to the center of the constriction, the magneto-mechanical oscillator device 32 measures the difference between static pressures between inside and outside of the constriction, which is related to flow. This is an embodiment of the bronchial sensor device 10 as a Venturi meter.

Figure 4:
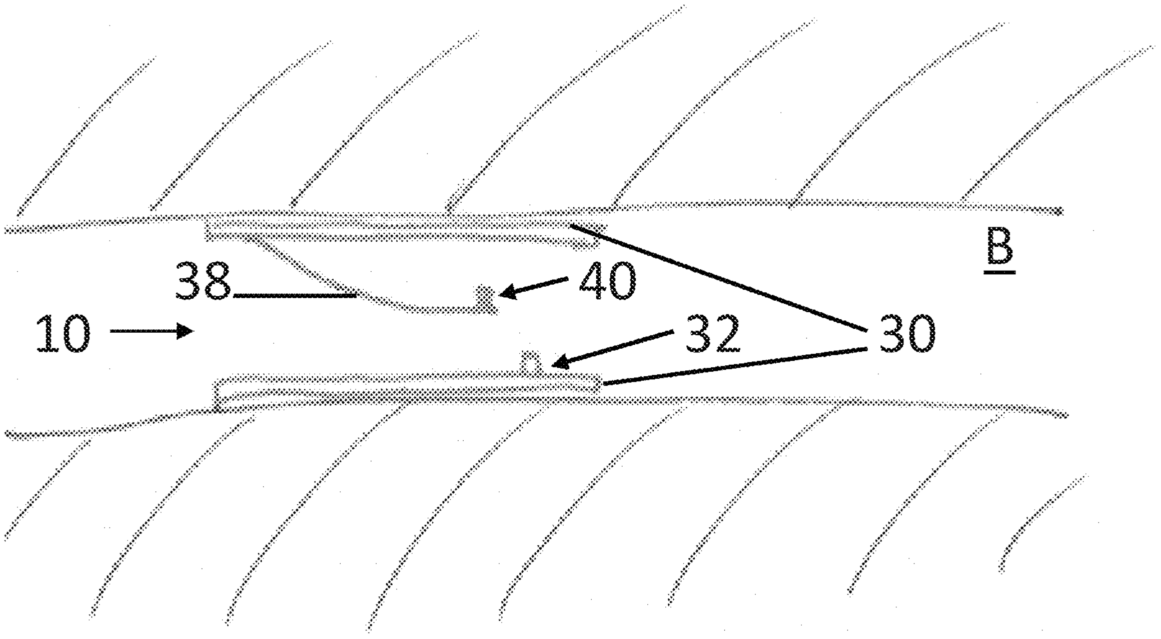

FIG. 4 shows another example of the bronchial sensor device 10. As shown in FIG. 4, the bronchial sensor device 10 is disposed in the bronchus B of the patient P. The bronchial sensor device 10 includes a deflecting membrane 38 attached to the stent 30 and configured to move based on fluid flow changes in the bronchus B. A magnet (i.e., a permanent magnet 40) is disposed on the deflecting membrane 38. Each magneto-mechanical oscillator device 32 is configured to measure a pressure difference based on a measured distance between each magneto-mechanical oscillator device 32 and the magnet 40 during movement of the deflecting membrane 38 related to fluid flow in the bronchus B (see, e.g., US 2020/0400509, which is incorporated herein by reference in its entirety).

Yet another method is a configuration similar to a pitot tube where one micro-bot pressure sensor is used to measure the stagnation (or total) pressure and another micro-bot pressure sensor measures the static pressure. From Bernouill's equation the flow velocity-dependent dynamic pressure, and hence the flow velocity, can be calculated.

FIGS. 2-4 depict the bronchial sensor device 10 as a flow measurement device or a volume measurement device. For mechanical ventilation, it is of interest to measure the volume provided to the patient B or a region of the lung. If the time-flow curve is measured continuously as it is possible with the help of a flow measurement device, the flow can be integrated over time to get the volume which has been applied.

Figure 5:
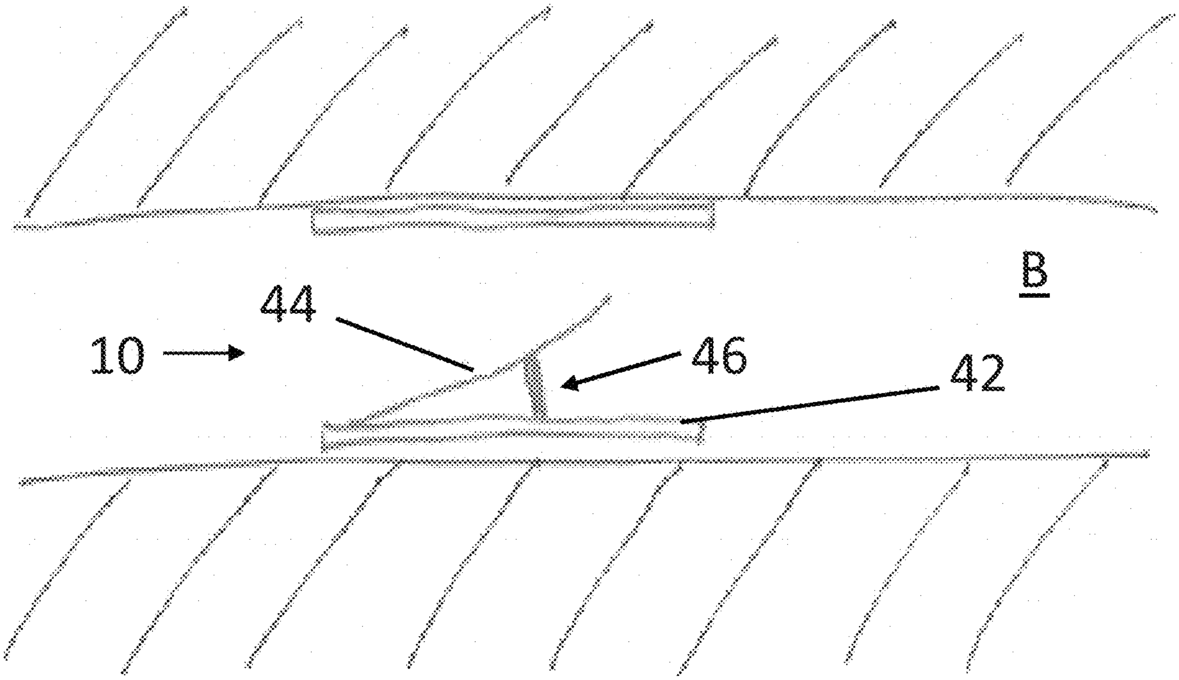

FIG. 5 shows an embodiment of the bronchial sensor device 10 configured to control or change the fluid flow. As shown in FIG. 5, the bronchial sensor device 10 includes a base 42, a membrane 44 with a hinged connection to the base 42, and an actuator 46 connected to the membrane 44. The membrane 44 and the actuator 46 can operate to create a variable constriction, and thus a variable sensor. The electronic controller 13 is configured to calculate the fluid flow based on a distance between the membrane 44 and the base 42 measured by the actuator 46. In some examples, the actuator 46 comprises a magnet (i.e., a rotating magnet actuated by spatially rotating fields on a simple gear mechanism to adjust an opening size of the constriction), and the electronic controller 13 is configured to calculate the fluid flow based on magnetic fields generated by the magnet 46. The actuator 46 can also be controlled by, for example, the measured fluid pressure in the bronchus, the calculated fluid flow measurement through the bronchus, a determined volume of fluid in the bronchus, a ventilation parameter of a mechanical ventilator (2), and other measured or determined parameters.

Figure 6A:
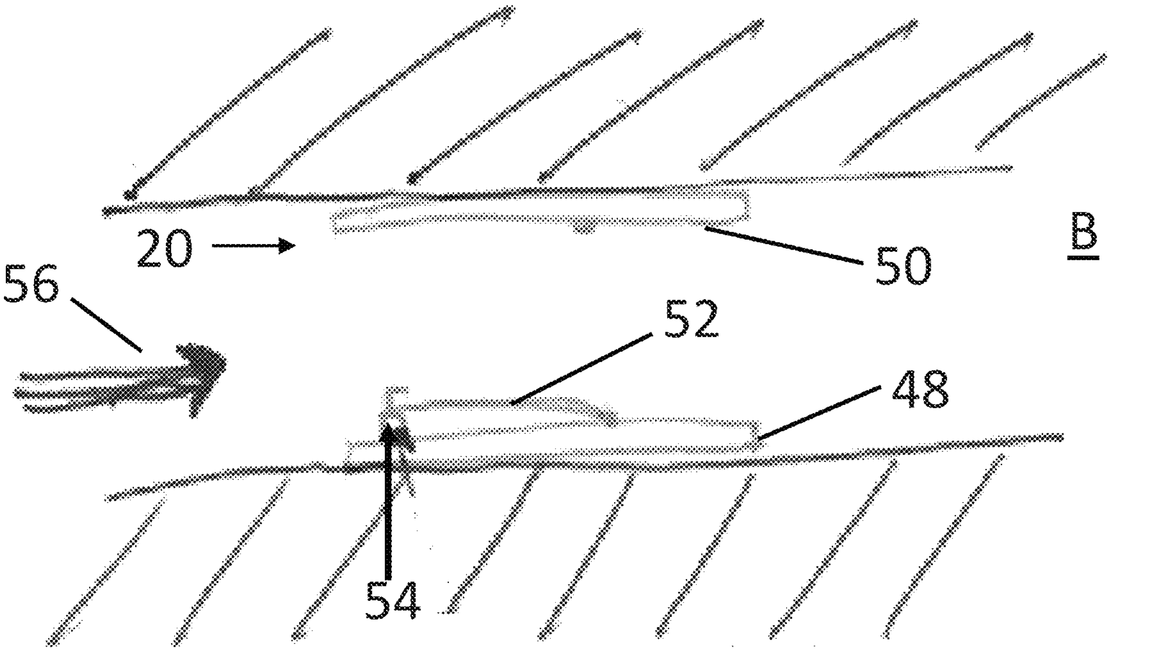
FIGS. 6A and 6B show an example of an actuator-controlled endobronchial valve.
Figure 6B:
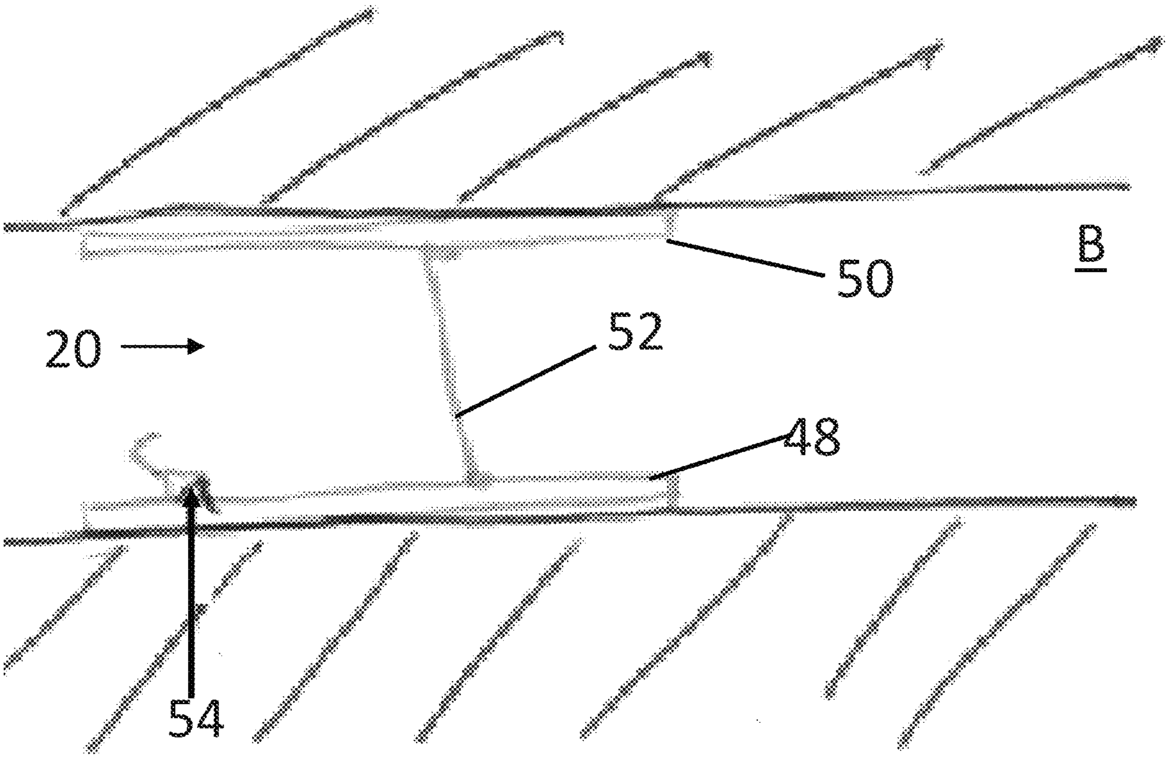

With reference to FIGS. 6A and 6B, some illustrative embodiments of the endobronchial valve 20 are described. In some embodiments, the endobronchial valve 20 can comprise a "active" endobronchial valve by controlling a portion of fluid flowing to the patient P.

The endobronchial valve 20 is configured to block a region of the lung, by blocking a bronchial tube that ordinarily passes a portion of the air delivered by the mechanical ventilator 2 to that lung region. As shown in FIGS. 6A and 6B, the endobronchial valve 20 can include a base comprising first and second strips 48, 50 configured to be disposed on opposing walls of the bronchus B. A membrane 52 has a pivot connection to the first strip 48. An actuator 54 (i.e., a magneto-mechanical oscillator device or other magneto-mechanical actuator) is connected to retain the valve in an open position by contacting and retaining the membrane 52 proximate to the second strip 50 as shown in FIG. 6A, and is operable to release the membrane 52 to close the valve in response to a magnetic control signal to close the valve, as shown in FIG. 6B. In some examples, the actuator 54 can hold back the membrane 52 in an open position (FIG. 6A) until the air flow pushes the actuator 54 to the second strip 50 (FIG. 6B). If this control device is combined with a pressure, flow, or volume sensor, it can be used to limit the maximal pressure, flow, or volume to the lung area of interest. Appropriate safety mechanism can ensure that the valve does not close unintentionally. It is noted that the illustrative valve 20 is a two-position valve, and in the closed position (FIG. 6B) the air flow may be completely blocked (e.g., if the released membrane 52 completely closes of the lumen) or only partially blocked (e.g., if the membrane 52 has some openings, slits, or the like to allow some passage of air). Moreover, it will be appreciated that the illustrative endobronchial valve 20 of FIGS. 6A and 6B is merely a nonlimiting illustrative example, and other designs are contemplated. For example, there could be two or more (e.g. N) membranes 52 presenting different levels of gas flow resistance with a separate actuator for each membrane, and in this way the N-membrane valve can generate a range of different discrete flow resistance values.

Figure 7:
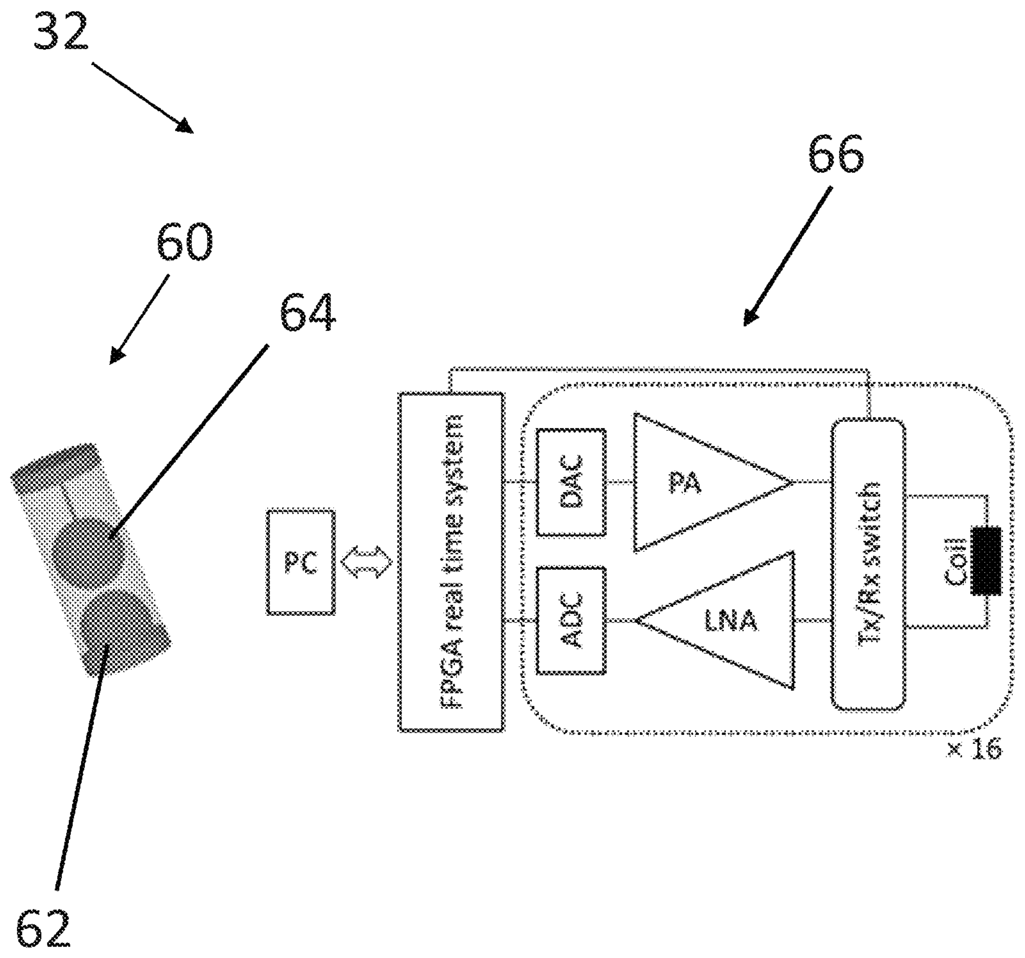
FIG. 7 shows an actuator device used in the system of FIG. 1.

FIG. 7 shows an example of a magneto-mechanical oscillator device 32. As shown in FIG. 7, the magneto-mechanical oscillator device 32 includes a resonator 60 comprising a passive device having a fixed magnet 62 and a suspended permanent magnet 64, where the suspended permanent magnet 64 performs a rotational oscillation in response to magnetic field pulses from the fixed magnet 62. The magneto-mechanical oscillator device 32 also includes a detection system 66 configured to generate excitation pulses (transmit channels, Tx) and receiving signal (Rx) from an array of up to 16 coils. The detection system 66 can also apply field sequences for controlling magnetically driven actuators (e.g. rotating fields for screw-based actuators).

In some embodiments, the bronchial sensor device 10 can include a membrane and an adjustable magneto-mechanical oscillator device with a simple gear mechanism that can be used to construct a valve which acts as a pressure regulator. This control device would adjust its opening automatically to limit the pressure to one or more portions of the lungs of the patient P. Once the measurement devices combined with control devices have been placed bronchoscopically in the bronchi, these devices are controlled in real-time with the help of a transceiver system to get signals to and from the magneto-mechanical oscillator devices. The signals from the measurement devices are analyzed with the help of a computer program, which calculates pressures, flows, and volumes. These values enter a model of the patient's lung either based on an individual CT scan or on the general knowledge of human anatomy.

The operator of the device 10 can adjust maximal pressure, maximal flow, maximal volume, etc. for each of the control devices in the lung regions of interest. In addition, the computer program controls the settings of a mechanical ventilator, which provides air pressure, flow, and volume through the trachea. Dynamic control of the devices is in particular interesting for handling dynamic ventilation problems like pendelluft by ensuring e.g. that air can flow only out during expiration and only in during inspiration.

As an example use case, alveolar overdistention is a condition which can lead to persistent lung damage after mechanical ventilation. To protect the lungs, a plateau pressure applied to small airways and alveoli during positive-pressure ventilation should be limited. The bronchial sensor device 10 allows for clinicians to measure the local pressure within one or more bronchi B of the patient P.

Since a local pressure is not necessarily the same as the pressure applied by the mechanical ventilator 2 at the endotracheal tube 16, local pressure measurements can be used to limit the local plateau pressure, for example, by changing the overall settings of the mechanical ventilator 2 in such a way that the overall plateau pressure at the endotracheal tube 16 is reduced. With this approach, not only the average plateau pressure (as measured by the mechanical ventilator 2), but also the local plateau pressures, do not exceed a predetermined threshold. For example, the maximum of the local pressure measurements can be used determine the optimal overall pressure by adapting the actual overall pressure (increasing or decreasing) until the maximum of the local pressure measurements has a certain target value.

Instead of measuring the local pressure, it is also possible to measure the local flow and (for example, by integrating flow over time) to measure the local tidal volume using the bronchial sensor device 10. Therefore, for each of the lung areas equipped with a bronchial sensor device 10 in the corresponding bronchus B, it is possible to measure the local tidal volume. If the local tidal volume exceeds a predetermined threshold, the overall tidal volume as applied by the mechanical ventilator 2 may be reduced until all measured local tidal volumes are below their thresholds.

To protect the lungs from local alveolar overdistention, one or more endobronchial valves 20 may be placed endobronchially in different bronchi B. These endobronchial valves 20 may contain the micro-bot actuators 54 configured to close a corresponding bronchus B triggered by an external signal applied to the micro-bot actuators 54. In addition, the endobronchial valves 20 may contain one or more micro-bot sensors 32,34 which measure local pressure and local flow.

The optimal local tidal volumes corresponding to the lung areas controlled by the endobronchial valves 20 may be determined based on a computed tomography (CT) scan or a digital model of a lung of the patient P. These optimal local tidal volumes are portions (i.e., percentages) of the overall tidal volume that the mechanical ventilator 2 delivers at the endotracheal tube 16. If the overall tidal volume is increased or decreased, these optimal local tidal volumes also change proportionally.

If during an inspiration the volume measurement at one of the endobronchial valves 20 exceeds the optimal local tidal volume, the micro-bot actuator 54 is triggered to close the endobronchial valve 20. Thereafter, a remainder of the overall tidal volume as delivered by the mechanical ventilator 2 would be distributed to the other lung areas, which have not reached their optimal tidal volume yet. The procedure would be repeated with the rest of the endobronchial valves 20 until, at the end of the inspiration (i.e., when the overall tidal volume is delivered by the mechanical ventilator 2), all lung areas behind the endobronchial valves 20 will have received their optimal tidal volume.

In some embodiments, instead of implanting active control devices, passive resistors or valves can be used. For example, passive resistors are simple stents with constrictions of a defined diameter. They can either be built with fixed diameter, and the resistor with the right diameter must be selected. Alternatively, resistors with adjustable constriction (and thus adjustable resistance) can be built. Their properties are set before implantation and as passive devices remain fixed until they are explanted. In another example, passive valves are similar to passive resistors. They open and close at a fixed (or adjustable and then fixed) pressure or flow.

In some embodiments, a computer program (e.g. a model comprising a Digital Twin of the patient) can be used to estimate the optimal selection or settings of the passive control devices.

In some embodiments, feedback can be provided to a clinician, such as feedback from functional imaging to adapt the control devices and/or feedback from wearables or patient monitors (e.g. vital sign measuring devices) to adapt the control devices.

The disclosure has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. A medical device for treating an associated patient, comprising:
- a bronchial sensor device configured to measure fluid pressure in a bronchus of the associated patient, the bronchial sensor device including:
  - a stent with pressure sensors disposed proximate to each end there of; and
  - a tube extending from one of the ends of the stent to a constriction in the stent; and
- an electronic controller configured to:
- receive a measured fluid pressure from the bronchial sensor device including a pressure difference between ends of the constriction in the stent; and
- calculate a fluid flow measurement through the bronchus based on the measured fluid pressure.

2. The medical device of claim 1,
- wherein the electronic controller is configured calculate the fluid flow measurement based on a diameter of the stent and the measured fluid pressure by the pressure sensors.

3. The medical device of claim 2, wherein each pressure sensor comprises a magneto-mechanical oscillator device.

4. The medical device of claim 3,
- wherein the magneto-mechanical oscillator device is configured to measure the pressure difference between the ends of the constriction in the stent.

5. The medical device of claim 3, further comprising:
- a deflecting membrane attached to the stent and configured to move based on fluid flow changes in the bronchus; and
- a magnet disposed on the deflecting membrane;
- wherein each magneto-mechanical oscillator device is configured to measure a pressure difference based on a distance between each magneto-mechanical oscillator device and the magnet during movement of the deflecting membrane.

6. The medical device of claim 1, further comprising:
- a mechanical ventilator configured to deliver mechanical ventilation to the associated patient;
- wherein at least one setting of the mechanical ventilator is controlled based on at least one of:
- the measured fluid pressure in the bronchus;
- the calculated fluid flow measurement through the bronchus; or
- a determined volume of fluid in the bronchus.

7. A medical device for treating an associated patient, comprising:
- a bronchial sensor device configured to measure fluid pressure in a bronchus of the associated patient, the bronchial sensor comprising:
  - a base;
  - a membrane with a hinged connection to the base; and
  - a magnet connected to the membrane; and
- an electronic controller configured to:
  - receive a measured fluid pressure from the bronchial sensor device;
  - receive a distance between the membrane and the base measured by the magnet; and
  - calculate a fluid flow measurement through the bronchus based on the measured fluid pressure and based on magnetic fields generated by the magnet.

8. A medical device for treating an associated patient, comprising:
- a bronchial sensor device configured to measure fluid pressure in a bronchus of the associated patient; and
- a bronchial valve including:
- a base comprising first and second strips configured to be disposed on opposing walls of the bronchus;
- a membrane with a pivot connection to the first strip;
- a magneto-mechanical actuator connected to the membrane;
- wherein the magneto-mechanical actuator is configured to retain the valve in an open position by contacting and retaining the membrane proximate to the second strip, and to close the valve by releasing the second strip in response to a magnetic actuation signal; and
- an electronic controller configured to:
  - receive a measured fluid pressure from the bronchial sensor device; and calculate a fluid flow measurement through the bronchus based on the measured fluid pressure.

* * * * *